(12) United States Patent
Portney

(10) Patent No.: US 11,846,832 B2
(45) Date of Patent: Dec. 19, 2023

(54) PRESBYOPIA CORRECTION WITH INDIVIDUAL PERFORMANCE OPTIMIZATION

(71) Applicant: Valdemar Portney, Newport Coast, CA (US)

(72) Inventor: Valdemar Portney, Newport Coast, CA (US)

( * ) Notice: Subject to any disclaimer, the term of this patent is extended or adjusted under 35 U.S.C. 154(b) by 812 days.

(21) Appl. No.: 16/947,333

(22) Filed: Jul. 29, 2020

(65) Prior Publication Data

US 2021/0236270 A1 Aug. 5, 2021

Related U.S. Application Data

(60) Provisional application No. 62/983,753, filed on Mar. 2, 2020, provisional application No. 62/981,534, filed on Feb. 26, 2020, provisional application No. 62/970,100, filed on Feb. 4, 2020.

(51) Int. Cl.
| | |
|---|---|
| *A61F 2/16* | (2006.01) |
| *G02C 7/08* | (2006.01) |
| *G02C 7/04* | (2006.01) |
| *G02B 27/00* | (2006.01) |
| *A61F 2/48* | (2006.01) |
| *A61B 3/113* | (2006.01) |

(52) U.S. Cl.
CPC ............ *G02C 7/083* (2013.01); *A61F 2/1624* (2013.01); *A61F 2/1635* (2013.01); *G02B 27/0093* (2013.01); *G02C 7/041* (2013.01); *A61B 3/113* (2013.01); *A61F 2/482* (2021.08); *A61F 2240/008* (2013.01); *A61F 2250/0001* (2013.01); *A61F 2250/0002* (2013.01)

(58) Field of Classification Search
CPC .... G02C 7/083; G02C 7/041; G02B 27/0093; A61F 2/1624; A61F 2/1635; A61F 2/482; A61F 2240/008; A61F 2250/0001; A61F 2250/0002; A61B 3/113
USPC ........................................................ 351/219
See application file for complete search history.

(56) References Cited

U.S. PATENT DOCUMENTS

| | | | |
|---|---|---|---|
| 8,096,654 | B2 | 1/2012 | Amirparviz et al. |
| 9,364,319 | B2 | 6/2016 | Portney |
| 9,500,884 | B2 | 11/2016 | Egan et al. |
| 9,931,203 | B2 | 4/2018 | Portney |
| 10,076,408 | B2 | 9/2018 | Basinger et al. |
| 10,285,805 | B2 | 5/2019 | de Juan, Jr. et al. |
| 10,409,092 | B1 | 9/2019 | Youssef |

(Continued)

*Primary Examiner* — Joseph P Martinez
*Assistant Examiner* — Grant A Gagnon
(74) *Attorney, Agent, or Firm* — Orbit IP

(57) ABSTRACT

A presbyopia correcting system includes a test lens assembly, a controller and a dynamic lens assembly. The test lens assembly is disposed within or on an eye of a patient and includes measuring device, a transmitter and a first supporting member. The measuring device measures a pressure exerted by an ocular element of the eye and then transmits the data to the controller. A medical provider can then select an appropriate dynamic lens assembly to replace the test lens assembly. The dynamic lens assembly includes a presbyopia correcting optical element configured to change a focus with the pressure exerted by the ocular element of the eye. The dynamic lens assembly also has a second supporting member that is identical to the first supporting member. Replacing the test lens assembly with the dynamic lens assembly then corrects the presbyopia condition of or provide low vision magnification for the patient.

22 Claims, 4 Drawing Sheets

(56) References Cited

U.S. PATENT DOCUMENTS

| | | |
|---|---|---|
| 10,463,473 B2 | 11/2019 | Rombach |
| 10,485,654 B2 | 11/2019 | Brady et al. |
| 10,548,718 B2 | 2/2020 | Salahieh et al. |
| 10,561,492 B2 | 2/2020 | Galstian et al. |
| 10,602,513 B2 | 3/2020 | Winoto |

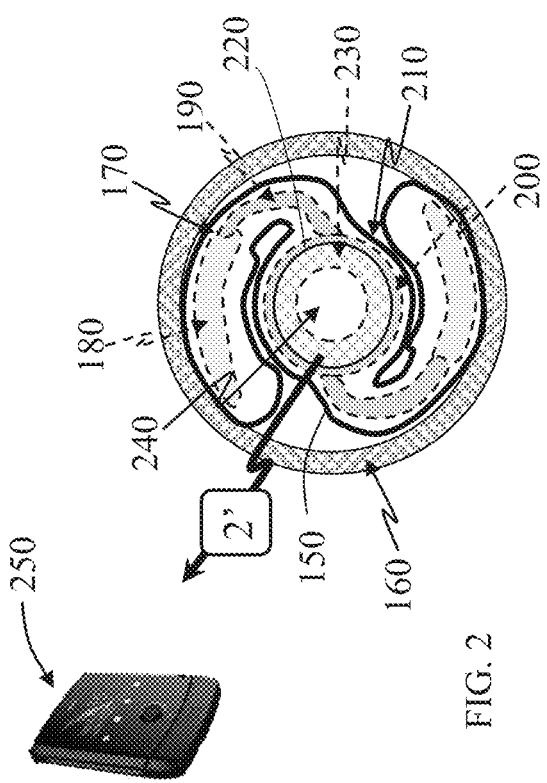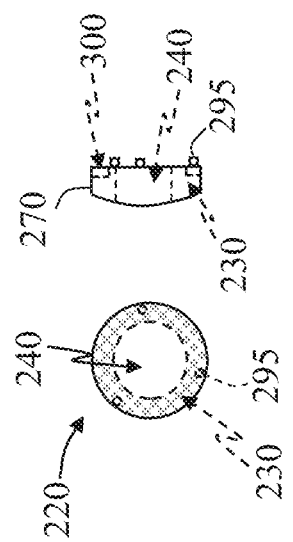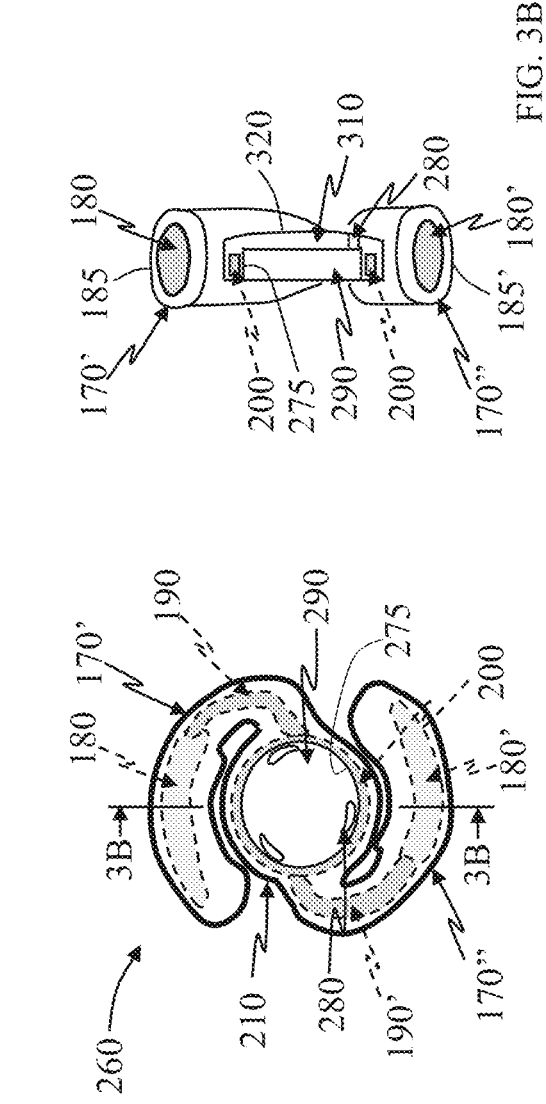

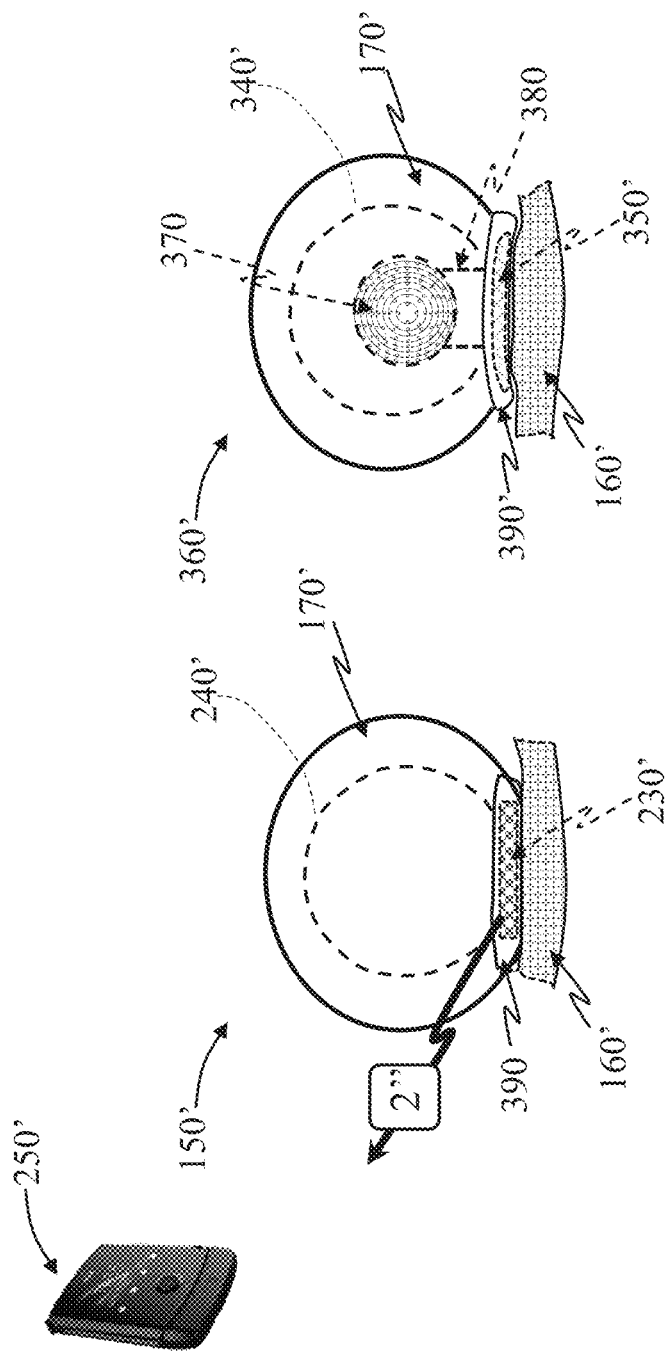

PRESBYOPIA CORRECTION WITH INDIVIDUAL PERFORMANCE OPTIMIZATION

CROSS-REFERENCE TO RELATED APPLICATIONS

This non-provisional application claims priority from U.S. Provisional Patent Applications: Ser. No. 62/970,100 filed Feb. 4, 2020; Ser. No. 62/981,534 filed Feb. 26, 2020; and Ser. No. 62/983,753 filed Mar. 2, 2020, the entire contents of which all applications are fully incorporated into the present application with this reference.

DESCRIPTION

Field of the Invention

The present invention relates generally to a presbyopia correcting lens that changes its optical power with a surface shape or relative movement of lens parts under the action of an ocular element of the eye. More particularly, it relates to a presbyopia correcting system of test intraocular lens (IOL) and presbyopia correcting IOL, and a presbyopia correcting system of test contact lens (CL) and presbyopia correcting CL The invention also relates to low vision application by applying magnification for patients with macular problems. In addition, the present invention relates to a wireless communication of test IOL and test CL with external electronic device (controller) to transfer pressure characteristics exerted on the test lens by an ocular element of the eye to allow a selection of presbyopia correcting IOL and presbyopia correcting CL with individual performance optimization.

BACKGROUND OF THE INVENTION

Ophthalmic lenses disclosed in this application refer to an intraocular lens (IOL) that is installed inside the eye and to a contact lens (CL) that is installed over the front surface of the eye.

A development of an ophthalmic lens with a variable foci has been a subject of many innovations. Fluidic balloon type IOL where optical power varies with stretching and squeezing fluidic balloon, is described by Salahieh, et al. in U.S. Pat. No. 10,548,718, Brady, et al. in U.S. Pat. No. 10,485,654, de Juan, Jr., et al. in U.S. Pat. No. 10,285,805, the contents of which are incorporated in full herein with this reference. Supporting element and optical body of fluidic balloon IOL have been described as one piece or modular two-piece structure where the optical body is a replaceable part. The fluidic balloon application to contact lens (CL) has been described by Egan, et al. in the U.S. Pat. No. 9,500,884, for instance, the contents of which are incorporated in full herein with this reference.

Alvarez type IOL design where wave plates are mutually shifting perpendicularly to the optical axis, is described by Rombach, et al. in the U.S. Pat. No. 10,463,473, the contents of which are incorporated in full herein with this reference. This type of IOL and fluidic balloon IOL are called accommodating IOLs (AIOL). Fluidic balloon type contact lens is called adjustable or variable CL. Both AIOL and variable CL designs are called "analog ophthalmic lenses."

Switching between refractive and diffractive surface shapes to create a binary system of two optical powers is described by Portney in the U.S. Pat. No. 9,364,319 for application to IOL, contact lens and eyeglasses, the contents of which are incorporated in full herein with this reference. The lens design is called switchable ophthalmic lens or "digital ophthalmic lens."

Accommodating and switchable IOL are called "dynamic IOL," and variable and switchable CL are called "dynamic CL." Analog and digital ophthalmic lenses together are called "dynamic lenses" as their optical powers are dynamically changing within certain range within a finite optical area, usually 3-5 millimeters diameter of an optical body.

Wireless communication of a dynamic lens with an electronic device has been described by Winoto in the U.S. Pat. No. 10,602,513, Amirparviz, et al. in the U.S. Pat. No. 8,096,654, the contents of which are incorporated in full herein with this reference. Portney in the U.S. Pat. No. 9,931,203, Youssef in the U.S. Pat. No. 10,409,092, Basinger, et al. in the U.S. Pat. No. 10,076,408, Galstian, et al. in the U.S. Pat. No. 10,561,492 disclosed electronic IOL and CL wirelessly communicating with external electronics, and they include a sensor to determine when and how much to accommodate thus achieving individual performance optimization for presbyopia correction, the contents of which are incorporated in full herein with this reference. Nevertheless, the issue remains that an electronic IOL is expensive and requires certain sizing for placing many non-optical parts which might be a challenge. This would also increase an incision size for the implantation, it also requires periodic eye surgery for power source replacement or the use of inductive charging which is cumbersome and requires additional electronics at the lens including an antenna. Critically, it involves constant communication between the sensor and activation mechanism of corresponding IOL to provide accommodation and dis-accommodation which places more strain on a power source, electronics reliability and potential interference with other wireless sources. Electronic CL is too expensive for implementation for presbyopia correction and has been described for other than presbyopia correcting applications such as drug delivery and measurement of disease conditions (diabetes, etc.) which is more justifiable of the cost involved.

In case of non-electronic dynamic lens, the central problem is the absence of individual performance optimization for presbyopia correction or low vision application by magnification. In case of a dynamic IOL, a force exerted by ciliary muscle to change an optical power is unknown for a given individual. The common approach is to run several trials to come up with acceptable efficacy of a non-electronic dynamic IOL but even then, there is no a guaranty that the IOL will provide the target range of powers in case of analog dynamic IOL or provide switching between the powers in case of digital dynamic IOL. Many factors influence a pressure exerted on the IOL beside the design itself, such as IOL placement inside the eye, circumference of ciliary body where ciliary muscle is located and other individual ocular factors. A effect of ciliary muscle action might be such that a pressure exerted by ciliary muscle for accommodation is too small for the dynamic IOL to achieve near power; or a fluctuation of pressure at ciliary muscle at dis-accommodation state is too large for the dynamic IOL which can result in unwanted intermediate or near power even with the far object viewing, i.e. no one can presume with full certainty that an object at certain distance would be in-focus, the outcome is only based on a probability.

Similar issue exists with a dynamic CL, though CL has an advantage over IOL by easy replacement to conceptually allowing for a try and error in optimum CL selection by increment fashion. Nevertheless, a process of prescribing an optimum CL is cumbersome and expensive as a wearer must wear each incrementally selected CL for several weeks to assess its performance and even then, such assessment remains highly subjective one. The process also involves multiple office visits and associated high cost.

On the other hand, non-electronic dynamic lens is relatively inexpensive as compared with an electronic dynamic lens, it is easier to install, no additional need to maintain electric power source and it offers a highly reliable construction because of its purely mechanical nature.

Thus, it would be desirable to provide method and devices which address the above deficiency and weaknesses of electronic and non-electronic dynamic lenses in achieving individual performance optimization for presbyopia correction that is effective and objective as offered by an electronic dynamic lens but inexpensive, fully reliable, easy to install and independent to extraneous factors such as electric power and wireless communication as offered by a non-electronic dynamic lens.

SUMMARY OF THE INVENTION

A presbyopia correcting system in accordance with the present invention consists of a test lens, a dynamic lens and a controller. The test lens and dynamic lens may be an IOL and/or a CL. Correspondently, a test IOL and dynamic IOL together with a controller form an "IOL presbyopia correcting system," or a test CL and dynamic CL together with a controller form a "CL presbyopia correcting system." A similar correcting system can be applied to low vision by magnification where a power difference between dioptric powers at refractive and diffractive states, so called Add power, is larger than a common Add power applied to presbyopia correction. The latter is commonly up to about 3 D (D stands for diopter) in spectacle plane and low vision magnification is about 5 D-10 D to provide 1.5×-2.5× magnification, though Add power might be even higher to provide higher magnification but the corresponding reduction in reading distance becomes a limiting factor. As the only difference between presbyopia correction and low vision magnification is the difference in Add powers in switching between the optical states, the reference only to presbyopia correction will be used hereafter with the understanding that it includes also a low vision magnification.

Test lens and dynamic lens include "supporting member" which is responsible for lens installation at the eye. The supporting members of a test lens and dynamic lens of the same presbyopia correcting system are identical in terms of their external attributes such as overall dimensions, shape, material and elastic characteristics.

Besides supporting member, a test IOL includes "IOL test member" consisting of (1) "measuring device" that includes pressure sensor to measure a pressure value exerted by an "ocular member" on the test lens and an emitter to wirelessly transmit the pressure value in a form of pressure data to a controller, and (2) "test IOL optical element" to provide imaging by the test IOLs at a focal distance, usually at far, upon the test IOL installation. Supporting member of the test IOL and dynamic IOL are designed to interact with ciliary body defined as ocular element for an IOL presbyopia correcting system. Ciliary muscle inside the ciliary body contracts during accommodation when the IOL wearer focusing on near object. In this condition a pressure by the ocular element on the supporting member increases. As the ciliary muscle relaxes for dis-accommodation when the IOL focuses on far object, the pressure by the ocular element on the supporting member reduces.

In a preferred embodiment of the present invention, a test IOL is of modular two-piece construction with detachable IOL test member (first part or first module) from the "remnant test IOL" (second part or second module). The remnant test IOL includes supporting member. In another preferred embodiment of the present invention, dynamic IOL of the same IOL presbyopia correcting system also is a modular two-piece construction consisting of "IOL presbyopia correcting member" (first part or first module) and "remnant dynamic IOL" (second part or second module). IOL presbyopia correcting member includes "IOL presbyopia correcting optical element" that changes IOUs optical power for presbyopia correction under interaction with the ocular element responsible for exerting pressure on the dynamic IOL.

The central aspect of the present invention is that the supporting members of the test IOL and dynamic IOL are totally identical. IOL presbyopia correcting member is dimensionally, shape wise largely identical to the IOL test member to allow for a replacement of the IOL test member with the IOL presbyopia correcting member thus replacing a test IOL with a dynamic IOL of the same IOL presbyopia correcting system without any disturbance to the remnant test IOL that includes the supporting member. As a result, IOL presbyopia correcting optical element replaces test IOL optical element precisely at the same location inside the eye and under the same interaction with the ciliary muscle.

A refractive sphero-cylinder error measured with IOL test lens installed is corrected by the IOL presbyopia correcting member when replacing the IOL test member. A refractive sphero-cylinder error is measured during the process of pressure measurements by the measuring device in order to include a corresponding refractive correction when running test protocol for pressure values. Both IOL test member of the test IOL and IOL presbyopia correcting member of dynamic IOL are preferred to be foldable for small eye incision to allow maintaining the eye's refraction.

Test CL has a single piece construction with supporting member including a prism ballast with truncating for interacting with lower eyelid defined as ocular element for CL presbyopia correcting system. A pressure from the ocular element increases with a wearer looks down to focus on near object and reduces with the wearer looks straight ahead. CL measuring device that includes pressure sensor is located at the ballast to measure a pressure value exerted by the ocular element on the test CL ballast. The CL measuring device also includes emitter to wirelessly transmit the pressure value in a form of pressure data to a controller.

Besides the ballast, the supporting member includes others features such as thin zones (also known as double slab-off) for effective interaction with the lower eyelid as well as for maintaining test CL orientation on the eye. The features are commonly used in translating (alternating) contact lenses. The overall sizing is like one used in segmented and progressive CL designs to ensure good centration and minimum displacement. In overall, such external attributes are well established in contact lens designs and applied to the test CL.

In a preferred embodiment of the present invention, test CL consist of two parts—supporting member to support test CL over the eye and test CL optical element to provide imaging for the test CL wearer. The test CL optical element is within the supporting member. A dynamic CL of the same CL presbyopia correcting system also consists of two parts—supporting member that is identical to the supporting member of the test CL in terms of external attributes such as the overall dimensions, shape, material and elastic characteristics, and CL presbyopia correcting optical element where the optical power change takes place during interaction of the dynamic CL with the ocular element.

Generally, a test IOL optical element and test CL optical element are called "test lens optical element" of a test lens, and IOL presbyopia correcting optical element and CL presbyopia correcting optical element are called "presbyopia correcting optical element" of a dynamic lens.

A controller collects pressure data emitted by a measuring device on the interaction of a test lens with an ocular element responsible for optical power change in corresponding dynamic lens. A pressure data can be collected intra-operatively or within a pre-programmed period of time post-operatively, say few months in case of test IOL that covers full eye healing upon test IOL installation or few weeks in case of test CL to cover wearer's acclimation to test CL wear. The preferable option is to collect refraction and pressure data intra-operatively where refraction is measured by wavefront aberrometer, the Optiwave Refractive Analysis (ORA) System for instance, or other technique, and pressure data is collected by effecting the ciliary muscle by pharmaceutical means, pilocarpine-induced ciliary muscle contraction for instance. In this case the replacement of the IOL test member with IOL presbyopia correcting member is performed during a single surgery. Another option is to have a second office visit where a medical provider runs a test protocol for a wearer of the test lens to view objects at different distances from far to near, collect data at the controller on pressure values exerted by corresponding ocular element on the measuring device and wirelessly communicated to the controller. In latter option the medical provides may have the controller to signal the measuring device to initiate and stop the measurements and start transmitting pressure data to the controller. Based upon collected and analyzed pressure data, the medical provider has the objective information on the interaction of the ocular element with test lens to allow objective selection of optimum dynamic lens for the wearer. Multiple runs of the test protocol to collect statistics on exerted pressure values is helpful for precisely optimizing individual performance of the dynamic lens. The medical provider also collects refraction information with test lens during the office vision to be included with the corresponding dynamic lens. The medical provider then replaces IOL test member with optimum IOL presbyopia correcting member or test CL with dynamic CL that is optimum for a given wearer.

In case of an analog dynamic lens, the optimization is defined as a synchronization between the pressure values exerted by ocular element on analog dynamic lens and measured by the test lens with wearer's focusing on far and near objects. As a result, the analog dynamic lens manifests far and near foci at the corresponding pressure values to bring in-focus far and near objects. In case of a digital dynamic lens, the optimization is defined as a selection of a pressure threshold for switching between far and near foci that is within the pressure values exerted by ocular element on digital dynamic lens and measured by the test lens with wearer's effort to focus on far and near objects. Such pressure threshold is somewhere in a middle of the pressure values range to provide reliable switching between far and near foci for optimized switchable dynamic lens of a given wearer.

Thus, a presbyopia correcting system includes a test lens that is analogous to electronic dynamic lens that offers effectiveness and objectivity in measuring pressure values used by the lens presbyopia correcting optics in providing target foci, and dynamic lens that is analogous to a non-electronic dynamic lens that is inexpensive, easier to install, no additional effort on maintaining electric power source and with highly reliable construction. A medical provider maintains a set of reusable IOL test members for intraocular lens application and reusable test CL for contact lens application to keep the overall cost of prescribing optimum dynamic lens down. Thus, the resulted presbyopia correcting system combines the benefits of both electronic and non-electronic lenses in providing individual performance optimization for presbyopia correction by intraocular and contact lens platforms.

In one of the embodiments of the present invention, a dynamic lens is designed with the stable state allocated to far focus, i.e. the dynamic lens optics takes the stable configuration that provides far focus if no or minimum pressure is applied by the ocular element. In this case, it might be adequate just to measure a power value for near focus and transmit it in a form of pressure data to the controller.

The preferred embodiment of the present invention references to a non-electronic dynamic lens but the method of individual performance optimization for presbyopia correction per present invention may also be applied to a dynamic lens with electro-active material used for optical power switching with an electric field. Liquid crystal material is one such electro-active materials. In this case some electronics is required for dynamic lens to create electric field, but it is simplified with the absence of external signal receiver and/or emitter.

Features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 shows a front view of the installed in the eye modular two-part test IOL and its communication with a controller.

FIG. 3A shows a front view of remnant test IOL which is one part of modular two-part test IOL. This part includes supporting member to respond to pressure by the ocular element when focusing on far and near objects.

FIG. 3B shows side view of the remnant test IOL of the FIG. 3A.

FIG. 4A shows a front view of IOL test member which is another part of modular two-part test IOL. This part includes measuring device to measure a pressure value exerted by the ocular element on the test IOL and transmit corresponding pressure data to a controller, and test IOL optical element to allow imaging by the test IOL.

FIG. 4B shows a side view of IOL test member of the FIG. 4A.

FIG. 7 shows a front view of the installed over the front surface of the eye two-part test CL that includes supporting member to respond to pressure by the ocular element when focusing on far and near objects. The supporting member includes measuring device to measure pressure values exerted by the ocular element on the test CL and transmit the corresponding pressure data to a controller. The test CL also includes test CL optical element to allow imaging by the test CL.

FIG. 8 shows a front view of the installed over the front surface of the eye two-part dynamic CL in place of the test CL of the FIG. 7. Dynamic IOL includes supporting member that is identical to one of the test CL except the measuring device being replaced by an actuation chamber. It also includes CL presbyopia correcting optical element in place of test CL optical element of the test CL.

DETAILED DESCRIPTION OF THE PREFERRED EMBODIMENTS

Figure 1:
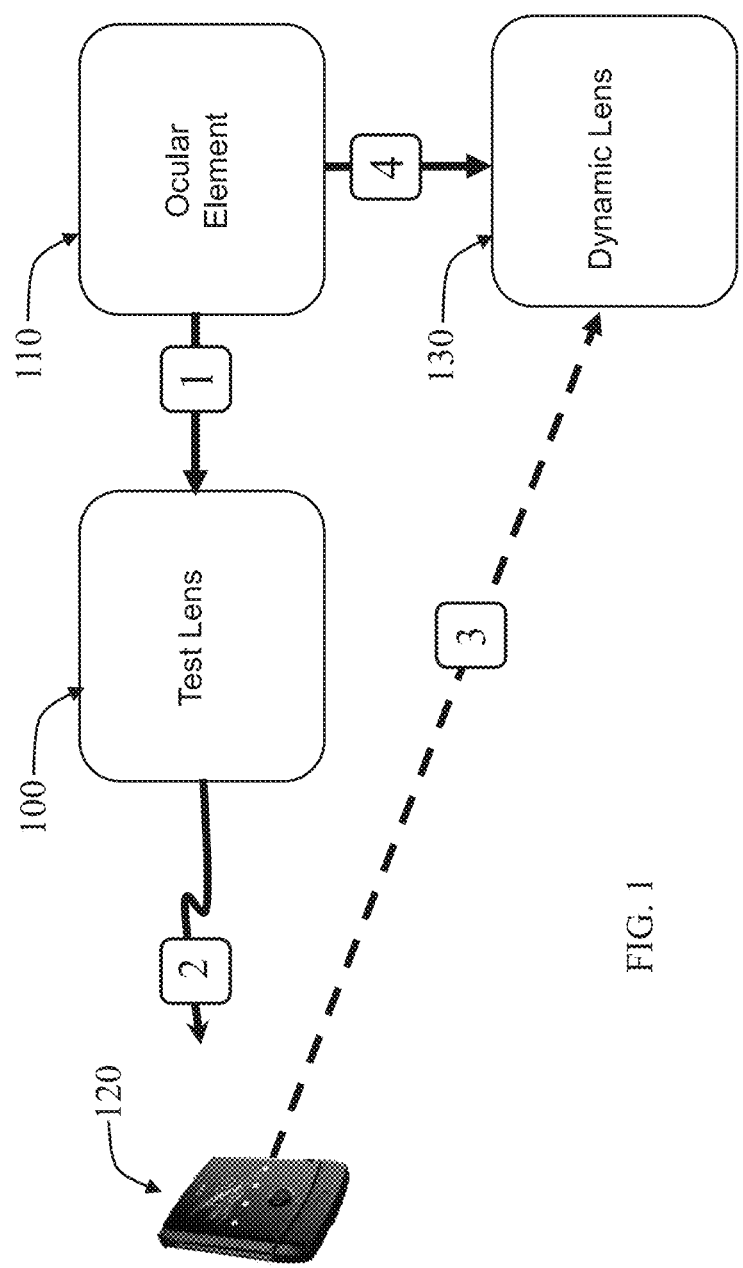
FIG. 1 shows a block diagram of individual performance optimization method by the presbyopia correcting system consisting of test lens, dynamic lens and external electronic device (controller) as a receiver of wireless signal from the test lens which is used for selecting optimum dynamic lens.

FIG. 1 demonstrates a block diagram of individual performance optimization method by the presbyopia correcting system consisting of test lens 100, dynamic lens 130 and external electronic device (controller) 120. Test lens 100 incorporates design and features of an electronic ophthalmic lens for presbyopia correction in a form of IOL and CL for measuring a pressure value exerted by an ocular element 110 when viewing objects at far and near distances, as shown by line 1. Ocular element is ciliary body with ciliary muscle inside in case of IOL and lower eyelid in case of CL. A pressure value is converted to pressure data and wirelessly transmitted by the measuring device of the test lens 100 to an external controller 120 as shown by line 2. Wireless communication may be in a form of Bluetooth, Li-Fi, Wi-Fi via local or cloud network. Controller can be a stand-alone electronic device, smartphone, smart device or the like with the corresponding application running thereon.

The pressure data collected by the controller 120 is analyzed by a medical provider to select optimum dynamic lens 130 as shown by line 3. Dynamic lens 130 is non-electronic version of a non-electronic ophthalmic lens for presbyopia correction in a form of IOL and CL. It includes presbyopia correcting optic that manifests far and near foci under the pressure values exerted by the ocular element 110 as shown by line 4. The dynamic lens 130 has become an optimized dynamic lens for a wearer. The use of "optimized" means that pressure values exerted by the ocular element 110 on the dynamic lens 130 create far and near foci by the optimized dynamic lens 130 that bring far and near objects viewed with test lens 100 in-focus.

FIG. 2 is a front view showing a controller 250 installed in the eye as a modular two-part test IOL 150 that communicates with the controller 250 as shown by line 2'. The test IOL 150 includes supporting member 170 to support the test IOL 150 inside the eye by the ocular element 160. The ocular element 160 consists of ciliary body with ciliary muscle inside. One part of the test IOL 150 is IOL test member 220 placed within the remnant optical body 210 connected to the supporting member 170. Remnant optical body 210 and supporting member 170 form the second part of the test lens 150 called remnant test lens.

Regarding the supporting member, it could be one-element supporting member or multi-element supporting member, as in this case the supporting member 170 consists of two elements. Within the supporting member there are support chambers, with one support chamber 180 being labeled as shown in the FIG. 2. Both support chambers are connected to a connect chamber 200 within the remnant optical body 210. The test lens 150 interacts with ocular element 160. As the wearer of the test IOL 150 focuses on near object, the ciliary muscle contracts and the ocular element 160 increases a pressure on the supporting member 170. Some fluid in the support chambers is transferred to the connect chamber 200 via the channels at the supporting member 170. For instance, a fluid from support chamber 180 via channel 190 is transferred to the support chamber 200. The connect chamber 200 increases pressure on the IOL test member 220. The corresponding pressure is called a "pressure value for near." As the wearer focuses on a far object, the ciliary muscle relaxes, and the optical element reduces pressure on the supporting member 170. The fluid is now transferred in reverse from the connect chamber 200 to the support chambers thus reducing pressure on the IOL test member 220. The corresponding pressure is called a "pressure value for far." Together, the pressure for far and the pressure for near are called "pressure values."

IOL optical test member 220 is between 4-6 mm in diameter. It consists of measuring device 230 and test IOL optical element 240. Pressure values are measured by the measuring device 230 and converted to pressure data which is then transmitted to the controller 250 as shown by line 2'. The pressure sensor can be made very small, for instance a sensor that is thin (0.1 mm) and flexible such as those made by Tekscan®, or the sensor can be a capacitive flexible pressure sensor. Micro-electronics have also become better developed. To power the measuring device 230 one may use a thin film rechargeable solid-state smart batteries (SSB) by Cymbet™, such as the EnerChip™, for instance a millimeter-sized CBC910 can be integrated with microelectronics into a single package. Test IOL optical element 240 is another part of the IOL test member 220. It is about 3-4 mm in diameter and represents a sphero-cylinder optic that provides imaging by the test IOL for the wearer, usually for far. Thus, the test IOL optical element 240 has a spherical power and a cylinder in order to neutralize astigmatic refractive error. In this case, the test lens 150 becomes a toric IOL and is aligned its axis of cylinder correction to the axis of astigmatic error of the eye allowing a wearer to have acceptable vision with test IOL 150.

FIG. 3A demonstrates a front view of a remnant test lens 260 which is one part of the modular two-part test lens 150. It includes support member 170 consisting of support element 1, numbered 170', and support element 2, numbered 170". A support member can be of any shape and number of support elements. Support element 1 incorporates support chamber 180 and support element 2 incorporates support chamber 180', both responding to an interaction of the supporting member 170 with the ocular element 160 as described above. Both support chambers 180 and 180' are connected to the contact chamber 200 of the remnant optical body 210 via channels 190 and 190' correspondingly.

There is an opening 290 within the remnant optical body 210 separated from the support chamber by a thin flexible wall 275. The opening within the remnant optical body may be all the way through the opening or not through the opening 290 as shown at the remnant optical body 210. The opening 290 includes three through holes at the opening periphery close to the wall 275, where one of the holes is numbered 280. The shape of each hole widens at one end and narrows at the other end. The holes serve to drain the eye's aqueous or viscos used during implantation of the remnant test IOL 260 as the test IOL parts are implanted in sequence—first the remnant test lens 260 and then IOL test member 220. Both are made of a flexible material to be folded for small incision implantation. The holes may also serve for securing a placement of the IOL test member 220 at the opening 290 though different mechanisms which are possible.

FIG. 3B demonstrates a cross section of the test lens 260 shown on the FIG. 3A. It shows support element 1 numbed 170' with support chamber 180 encapsulated inside the support member by a thin flexible peripheral wall 185 at the periphery in order to respond to a pressure by the ocular element 160. The figure also shows support element 2 numbed as 170" with support chamber 180' encapsulated inside support member by a thin flexible peripheral wall 185'. FIG. 3B more clearly demonstrates the opening 290 shown with flat back surface and flat side wall 275. The side wall 275 may be slated and have features to secure IOL optical test member 220. There is posterior lens 310 shown with flat front surface and back convex surface 320. One drain and secure hole 280 through posterior lens 310 is also shown. Cross section of the support chamber 200 is shown encapsulated by side wall 275. The posterior surface 320 may be sphero-cylinder to correct for corneal astigmatism thus reducing a number of different IOL test members and IOL presbyopia correcting members required.

FIG. 4A demonstrates a front view of the IOL test member 220 consisting of measuring device 230 and test IOL optical element 240. There are three posts at the back of the IOL test member 220, one is numbered 295. The number of posts matches a number of through holes in the opening 290 where one hole was numbered 280 and one post was numbered 295. The posts are to be placed at the drain and secure holes of the remnant test lens 260 to secure the IOL optical test member 220 by slightly turning/rotating IOL test member 220 in order to press and secure the posts at the narrow sides of through holes.

FIG. 4B shows a side view of the IOL test member 220 of FIG. 4A and demonstrates measuring device 230, test IOL optical element 240 and posts on the back of the IOL test member 220, one of posts is numbered 295. There is recess 300 around IOL test member back periphery to assist with aqueous or viscos drainage during IOL test member 220 installation at the remnant test lens 260. The side periphery 270 is shown as a flat shape to match the shape of side wall 275 of the remnant test lens 260. Optionally, it might include a lubricious coating such as PEBAX® or Teflon™ to facilitate modular test IOL assembly. A side shape of an IOL test member is to compliment a shape of a side wall of a remnant test lens in a mirror fashion. The test IOL optical element 240 represented as a convex-plano optic which together with the posterior lens 280 are to provide test IOL optical power for focusing at the back of the eye for imaging. A test IOL optical element may be of different shapes, concave-plano or other optical shapes and the like which are required for imaging. Yet, it would be preferable to have a posterior surface 320 of the posterior lens 310 to manifest a variety of the shapes to minimize a number of IOL test members required.

Figure 5:
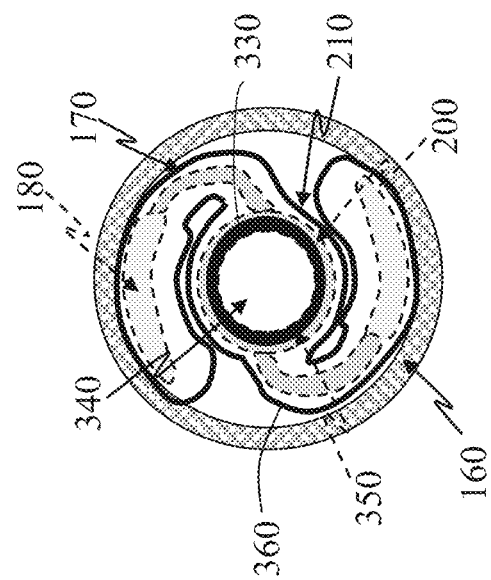
FIG. 5 shows a front view of the installed in the eye modular two-part dynamic IOL in place of the test IOL of the FIG. 2. Dynamic IOL includes supporting member that is identical to one of the test IOL. It also includes IOL presbyopia correcting member that replaced IOL test member.

FIG. 5 shows a front view of the modular two-part dynamic IOL 360 installed in the eye. One part of the dynamic IOL is IOL presbyopia correcting member 330 placed inside the remnant optical body 210 which is supported inside the eye by supporting member 170. The IOL presbyopia correcting member 330 has the same shape and dimensions as the IOL test member 220 which it replaces in the second step implementation. First step was the test IOL and IOL test member implantation. The dynamic IOL 360 interacts with the same ocular element 160 as the test IOL 150 as being supported by the same support member 170. Optimized dynamic IOL 360 produces in-focus vision when focusing on far and near objects because the exerted on it pressure values during accommodation and dis-accommodation are the same as measured by the test IOL 150 pressure values when focusing on far and near objects.

As the wearer looks at near object, ciliary muscle contracts and a pressure from the ocular element 160 on the support member 170 increases. The pressure pushes some fluid volume from the support chamber 180 into the contact chamber 200 to exert pressure on the actuation chamber 350 of the IOL presbyopia correcting member 330. In a preferred embodiment of the present invention, some fluid volume from it is transferred from the actuation chamber 350 into the IOL presbyopia correcting element 340 for switching optical element inside it into near optical power for near focus as described by Portney in U.S. Pat. No. 9,364,319. An IOL optical element make take different designs. For instance, it may take a form of a fluidic balloon to take place of actuation chamber 350 and IOL presbyopia correcting element 340. The corresponding fluidic balloon changes shape to produce far and near foci with the pressure values measured by the test IOL of the same IOL presbyopia correction system. Another option is to use an Alvarez type design as known to those skilled in the art where two wave plates replace the IOL optical element 340. A pressure value for near increases pressure on the actuation chamber to move one of the plates against the other plate to increase the optical power of the dynamic IOL for near focus. As the wearer looks at far object, ciliary muscle relaxes and a pressure from the ocular element 160 on the support member 170 reduces thus allowing for the presbyopia correcting member of any design to take its stable optical state of far focus.

The dynamic IOL 360 may also include a cylinder in addition to spherical power in order to effectively neutralize astigmatic refractive error. The cylinder may be included at the IOL presbyopia correcting member 330 and/or at the posterior lens 310 if partial opening 290 is applied. Any sphere or cylinder residual refractive error discovered with the test IOL 150 is included with an IOL presbyopia correcting member.

Figures 6A, 6B:
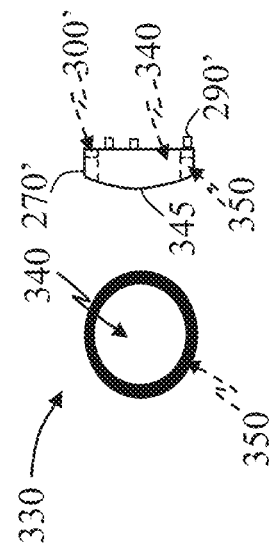
FIG. 6A shows a front view of IOL presbyopia correcting member that includes IOL presbyopia correcting optical element that changes optical power for presbyopia correction.
FIG. 6B shows a side view of IOL presbyopia correcting member of the FIG. 6A

FIG. 6A demonstrates a front view of the IOL presbyopia correcting member 330 which includes actuation chamber 350 and IOL presbyopia correcting element 340.

FIG. 6B shows a side view of the IOL presbyopia correcting member 330 with actuation chamber 350 and IOL presbyopia correcting element 340. The IOL presbyopia correcting member 330 has an identical external shape and dimensions of the IOL test member 220, except a central thickness might be different as well as a curvature of its front surface 345. Its side surface 270' is largely the same shape as 270 of the IOL test member 220 except a width. The IOL presbyopia correcting member 330 also includes identical posts at the back surface as the IOL test member 220 where one of the posts is numbered 290'. The IOL presbyopia correcting member 330 also includes peripheral recess 300' to assist with aqueous or viscos drainage during second step assembly of the dynamic IOL 360 when replacing IOL test member 220 with IOL presbyopia correcting member 330.

FIG. 7 shows a front view of the installed test CL 150' on the front surface of the eye and its communication with a controller 250' as shown by line 2". The test CL 150' consists of two parts, one is test CL optical element 240' of about 7 mm diameter and another is supporting member 170' which includes prism ballast 390 with truncation in combination with others features of the supporting member 170' such as thin zones (also known as double slab-off) and so on. The ballast 390 is for effective interaction with the lower eyelid 160' which is the ocular element for test CL and dynamic CL. The ballast 390 is also for maintaining test CL and dynamic CL orientations on the eye. The ballast is commonly used in translating (alternating) contact lenses. The overall sizing is similar to one used in segmented and progressive CL designs to insure good centration and minimum lens displacement.

A measuring device 230' is within the ballast 390 and a pressure value exerted on the measuring device 230' by the ocular element 160' is measured by a pressure sensor, converted to pressure data which is transmitted to the controller 250' as shown by line 2'. As the wearer of the test CL 150' focuses on a near object by looking down, the ocular element 160' increases pressure on the ballast 390 and measuring device inside. The corresponding pressure is called a "pressure value for near." As the wearer tries to see an object at far by looking straight ahead, the optical element 160' reduces pressure on the ballast 390 and measuring device inside. The corresponding pressure is called a "pressure value for far." Together, the pressure value for far and pressure value for near are called the "pressure values" which are measured and transmitted to the controller 250' in a form of pressure data. The pressure data is analyzed by a medical practitioner and provides for the selection of the optimum dynamic CL of the same CL presbyopia correcting system.

FIG. 8 describes a front view of the installed dynamic CL 360' that replaces the test CL 150' onto the eye. One part of the dynamic CL 360' is CL presbyopia correcting element 340' with the dimensions identical to test CL optical element 240' and another is supporting member 170' which is identical to the supporting member 170' of the test CL 150' in terms of their external attributes such as overall dimensions, shape, material and elastic characteristics. The only difference is that actuation chamber 350' at the ballast 390' of the dynamic CL 360' replaces measuring device 230' at the ballast 390 of the test CL 150' where ballast 390' is equivalent to ballast 390 in terms of shape, form and material.

The dynamic CL 360' interacts with the same ocular element 160' as in the test CL 150'. A pressure from the ocular element 160' on the ballast 390' changes within the same pressure values when the wearer of the optimized dynamic CL 360' looks straight ahead for far and down for near. In a preferred embodiment, the CL presbyopia correcting element 340' incorporates switchable optical element 370 described by Portney in the U.S. Pat. No. 9,364,319. Another option is for presbyopia correcting element include a fluidic balloon on place of switchable optical element 370 where it changes its shape for optical power change with the pressure values equivalent to those measured by the test CL. In another embodiment shown herein in FIG. 8, a presbyopia correcting element is connected with an activation chamber 350' by a channel 380. Some fluid volume from the actuation chamber 350' flows to the switchable optical element 370 with the wearer looking down thus switching the element 370 to near focus. Fluid flows back to the activation chamber 350' when the wearer is looking straight ahead and the switchable optical element takes its stable state for far focus. The corresponding optimized dynamic CL 360' produces in-focus vision when viewing far and near objects because exerted pressure values are the same as measured by the test CL 150'.

What is claimed is:

1. A presbyopia correcting system, comprising:
   a test lens having a measuring device, wherein the test lens is configured to be disposed within or on an eye of a patient, wherein the measuring device is configured to measure a pressure exerted by an ocular element of the eye, wherein the measuring device includes a transmitter configured to wirelessly transmit a pressure data regarding the pressure exerted by the ocular element of the eye when the test lens is disposed within or on the eye;
   a controller including a receiver, the receiver configured to receive the pressure data transmitted by the measuring device; and
   a dynamic lens having a presbyopia correcting optical element, wherein the dynamic lens is configured to be disposed within or on the eye in the same position as the test lens after the test lens has been removed partially or whole from the eye, wherein the presbyopia correcting optical element is configured to change a focus with the pressure exerted by the ocular element of the eye when the dynamic lens is disposed within or on the eye;
   wherein the test lens includes a first supporting member, the first supporting member configure to secure the test lens in a first position relative to the eye when the test lens is either installed inside the eye or installed over a front surface of the eye;
   wherein the dynamic lens includes a second supporting member, the second supporting member configured to secure the dynamic lens in the first position relative to the eye when the dynamic lens is either installed inside the eye or installed over the front surface of the eye; and
   wherein the second supporting member is identical in overall dimension, shape, material and elastic characteristic in comparison to the first supporting member.

2. The presbyopia correcting system of claim 1, wherein the test lens comprises a test lens ocular element configured to form an image at a back of the eye upon the test lens being disposed within or on the eye.

3. The presbyopia correcting system of claim 1, wherein the test lens is an intraocular lens.

4. The presbyopia correcting system of claim 2, wherein the dynamic lens is an intraocular lens.

5. The presbyopia correcting system of claim 3, wherein the ocular element of the eye is the ciliary muscle.

6. The presbyopia correcting system of claim 1, wherein the test lens is a contact lens.

7. The presbyopia correcting system of claim 6, wherein the dynamic lens is a contact lens.

8. The presbyopia correcting system of claim 7, wherein the ocular element of the eye is the lower eyelid.

9. A presbyopia correcting system, comprising:
   a) a test lens assembly configured to be disposed within or on an eye of a patient, the test lens assembly comprising:
      i) a measuring device, wherein the measuring device is configured to measure a pressure exerted by an ocular element of the eye when the test lens assembly is disposed within or on the eye of the patient;
      ii) a transmitter, wherein the transmitter is configured to wirelessly transmit a pressure data regarding the pressure exerted by the ocular element of the eye when the test lens is disposed within or on the eye of the patient;

iii) a first supporting member, wherein the first supporting member is configure to secure the test lens assembly in a first position relative to the eye when the test lens assembly is disposed within or on the eye of the patient;

iv) a test lens ocular element configured to form an image at a back of the eye upon the test lens assembly being disposed within or on the eye;

b) a controller including a receiver, the receiver configured to receive the pressure data transmitted by the measuring device; and c) a dynamic lens assembly configured to be disposed within or on the eye of the patient in a same position as the test lens assembly after the test lens assembly has been removed partially or whole from the eye of the patient, the dynamic lens assembly comprising:

i) a presbyopia correcting optical element configured to form an image at the back of the eye when the dynamic lens assembly is disposed within or on the eye of the patient;

ii) the presbyopia correcting optical element configured to change a focus with the pressure exerted by the ocular element of the eye when the dynamic lens assembly is disposed within or on the eye of the patient;

iii) a second supporting member, wherein the second supporting member is configured to secure the dynamic lens assembly in the first position relative to the eye when the dynamic lens is disposed within or on the eye of the patient;

iv) wherein the second supporting member is identical in overall dimension, shape, material and elastic characteristic in comparison to the first supporting member.

10. The presbyopia correcting system of claim 9, wherein the test lens assembly is an intraocular lens.

11. The presbyopia correcting system of claim 10, wherein the dynamic lens assembly is an intraocular lens.

12. The presbyopia correcting system of claim 11, wherein the ocular element of the eye is the ciliary muscle.

13. The presbyopia correcting system of claim 9, wherein the test lens assembly is a contact lens.

14. The presbyopia correcting system of claim 13, wherein the dynamic lens assembly is a contact lens.

15. The presbyopia correcting system of claim 14, wherein the ocular element of the eye is the lower eyelid.

16. A method of presbyopia correction optimization, the method comprising the steps of:

a) providing a test lens assembly configured to be disposed within or on an eye of a patient, the test lens assembly comprising:

i) a measuring device, wherein the measuring device is configured to measure a pressure exerted by an ocular element of the eye when the test lens assembly is disposed within or on the eye of the patient;

ii) a transmitter, wherein the transmitter is configured to wirelessly transmit a pressure data regarding the pressure exerted by the ocular element of the eye when the test lens is disposed within or on the eye of the patient;

iii) a first supporting member, wherein the first supporting member is configure to secure the test lens assembly in a first position relative to the eye when the test lens assembly is disposed within or on the eye of the patient;

b) providing a controller including a receiver, the receiver configured to receive the pressure data transmitted by the measuring device;

c) providing a dynamic lens assembly configured to be disposed within or on the eye of the patient in a same position as the test lens assembly after the test lens assembly has been removed whole or partially from the eye of the patient, the dynamic lens assembly comprising:

i) a presbyopia correcting optical element configured to form an image at the back of the eye upon the dynamic lens assembly being disposed within or on the eye of the patient;

ii) the presbyopia correcting optical element configured to change a focus with the pressure exerted by the ocular element of the eye when the dynamic lens assembly is disposed within or on the eye of the patient;

ii) a second supporting member, wherein the second supporting member is configured to secure the dynamic lens assembly in the first position relative to the eye when the dynamic lens is disposed within or on the eye of the patient;

iii) wherein the second supporting member is identical in overall dimension, shape, material and elastic characteristic in comparison to the first supporting member;

d) installing the test lens assembly within the eye of the patient;

e) collecting, with the controller, the pressure data from the measuring device;

f) selecting the dynamic lens assembly when evaluating the pressure data, wherein the dynamic lens assembly is configured to correct a presbyopia condition in the eye of the patient;

g) replacing the test lens assembly with the dynamic lens assembly.

17. The method of presbyopia correction optimization of claim 16, wherein the test lens assembly is an intraocular lens.

18. The method of presbyopia correction optimization of claim 17, wherein the dynamic lens assembly is an intraocular lens.

19. The method of presbyopia correction optimization of claim 18, wherein the ocular element of the eye is the ciliary muscle.

20. The method of presbyopia correction optimization of claim 16, wherein the test lens assembly is a contact lens.

21. The method of presbyopia correction optimization of claim 20, wherein the dynamic lens assembly is a contact lens.

22. The method of presbyopia correction optimization of claim 21, wherein the ocular element of the eye is the lower eyelid.

* * * * *